(12) United States Patent
Mitamura et al.

(10) Patent No.: US 11,306,160 B2
(45) Date of Patent: Apr. 19, 2022

(54) CURABLE COMPOSITION

(71) Applicant: MITSUI CHEMICALS, INC., Tokyo (JP)

(72) Inventors: Takenori Mitamura, Chiba (JP); Yoko Kosugi, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 16/753,086

(22) PCT Filed: Oct. 25, 2018

(86) PCT No.: PCT/JP2018/039650
§ 371 (c)(1),
(2) Date: Apr. 2, 2020

(87) PCT Pub. No.: WO2019/082964
PCT Pub. Date: May 2, 2019

(65) Prior Publication Data
US 2020/0291157 A1    Sep. 17, 2020

(30) Foreign Application Priority Data
Oct. 26, 2017 (JP) .............................. JP2017-207083

(51) Int. Cl.
| | |
|---|---|
| C08F 2/46 | (2006.01) |
| C08F 2/50 | (2006.01) |
| C08G 61/04 | (2006.01) |
| C08F 4/10 | (2006.01) |
| A61K 6/73 | (2020.01) |
| C08F 222/10 | (2006.01) |

(52) U.S. Cl.
CPC .................. *C08F 4/10* (2013.01); *A61K 6/73* (2020.01); *C08F 222/1065* (2020.02)

(58) Field of Classification Search
CPC .. A61K 6/00; A61K 6/887; A61K 6/73; C08F 220/28; C08F 4/40; C08F 222/22
USPC ................. 522/63, 6, 71, 189, 184, 1; 520/1
See application file for complete search history.

(56) References Cited

U.S. PATENT DOCUMENTS

| | | | |
|---|---|---|---|
| 9,511,004 B2 | 12/2016 | Naruse et al. | |
| 2003/0129521 A1* | 7/2003 | Matsumoto | G03F 7/029 430/138 |
| 2007/0040151 A1 | 2/2007 | Utterodt et al. | |
| 2012/0296003 A1 | 11/2012 | Naruse et al. | |
| 2015/0024141 A1* | 1/2015 | Shukla | C08J 3/28 427/510 |
| 2016/0175805 A1 | 6/2016 | Catchpole et al. | |
| 2016/0184143 A1 | 6/2016 | Hooi | |
| 2017/0309844 A1* | 10/2017 | Saeki | G03F 7/2022 |

FOREIGN PATENT DOCUMENTS

| | | | | |
|---|---|---|---|---|
| CN | 1083258 C | * | 4/2002 | ............. A61K 6/887 |
| CN | 101114034 | * | 1/2008 | |
| CN | 105101934 | * | 9/2017 | |
| JP | H09-157124 A | | 6/1997 | |
| JP | 2002-088108 A | | 3/2002 | |
| JP | 3449843 B2 | | 9/2003 | |
| JP | 2009-144054 A | | 7/2009 | |
| JP | 2009186758 | * | 8/2009 | |
| JP | 4646264 B1 | | 3/2011 | |
| JP | 2014-152107 A | | 8/2014 | |
| JP | 5683337 B2 | | 3/2015 | |
| JP | 5773557 B2 | | 9/2015 | |
| JP | 5846883 B2 | | 1/2016 | |
| JP | 2016-94482 A | | 5/2016 | |
| WO | 2012/157566 A1 | | 11/2012 | |
| WO | 2015/015220 A1 | | 2/2015 | |
| WO | 2015/015221 A1 | | 2/2015 | |

OTHER PUBLICATIONS

Hatanaka et al., CN 1083258C Machine Translation, Apr. 24, 2002 (Year: 2002).*
Kawashima et al, CN 105101934 Machine Translation, Sep. 22, 2017 (Year: 2017).*
Pia-Dalmau, 1-(2'-Hydroxyphenyl)benzothizoles, -benzoxazoles, and -benzoimidazoles for Plastic Scintillation applications, 1995, J. Org. Chern., 60, 5468-5473 (Year: 1995).*
Miki et al, JP 2009-186758 Machine Translation, Aug. 20, 2009 (Year: 2009).*
Takada, CN 101114034 Machine Translation, Jan. 30, 2008 (Year: 2008).*
English translation of International Search Report dated Jan. 22, 2019, by the Japanese Patent Office in corresponding International Patent Application No. PCT/JP2018/039650. (1 page).

* cited by examiner

*Primary Examiner* — Jessica Whiteley
(74) *Attorney, Agent, or Firm* — Buchanan Ingersoll & Rooney PC

(57) ABSTRACT

An object of the present invention is to provide a curable composition having sufficient polymerization properties even under acidic conditions. The curable composition of the present invention includes (a) a polymerizable monomer having an acidic group, (b) a transition metal compound, (c) at least one compound selected from benzoxazole compounds and benzothiazole compounds, and (d) a reducing agent.

19 Claims, No Drawings

CURABLE COMPOSITION

TECHNICAL FIELD

The present invention relates to a curable composition.

BACKGROUND ART

A technique for providing a curable composition by polymerizing a polymerizable monomer is widely used industrially. Specific examples thereof include thermal polymerization, photopolymerization, and ordinary temperature chemical polymerization, and those are carried out by methods according to the type of a polymerization catalyst blended in the composition including a polymerizable monomer. These polymerization methods are also widely used in the field of dental treatment, and are actually used as polymerization techniques for various adhesive materials and filler materials classified as resin-based restorative materials, such as dental adhesive resin cements, dental composite resins (including those having self-adhesive properties), dental adhesives, dental room-temperature polymerization resins, dental composite resins, dental backing materials, dental root fillers, orthodontic adhesives, mobile tooth fixing materials, and tooth fovea fissure sealant (dental sealant).

The main types of polymerization initiators contained in curable compositions widely used for dental treatment materials are photopolymerization initiators, which cause polymerization and curing through irradiation with visible light, and chemical polymerization initiators, which cause polymerization and curing by mixing two or more separately stored packs immediately before use, and cases using both initiators in combination in dental practice have also increased recently. Regarding the chemical polymerization initiator among these initiators, it is necessary to start the polymerization reaction only by mixing and kneading with the polymerization catalyst component at around ordinary temperature, and also to polymerize and cure the polymerizable monomer at around ordinary temperature, so that high polymerization activity is required as compared with other initiator systems.

An example of a common chemical polymerization initiator system widely used in the dental field is a redox polymerization initiator, which combines an oxidizing agent and a reducing agent. A curable composition containing a redox polymerization initiator is usually stored in the form of a plurality of compositions divided into a first pack including an oxidizing agent and a second pack including a reducing agent, so-called separately packed curable composition, until immediately before use. The chemical polymerization reaction is initiated by mixing the first pack and the second pack at the time of use, and the curing of the mixture proceeds. Accordingly, since combination of an oxidizing agent and a reducing agent capable of causing a redox reaction cannot usually be stored together in the same pack, there are some cases where the curable composition needs to be stored as a separately packed curable composition divided into three or more packs.

As a curable composition including a highly active chemical polymerization initiator, for example, a redox polymerization initiator system in which a peroxide and a reducing substance are combined is known and widely used in the field of dental materials. For example, a dental curable composition comprising a first pack containing a diacyl peroxide compound such as benzoyl peroxide as the peroxide and a second pack containing an aromatic amine compound as the reducing substance is known (Patent Literature 1). This curable composition containing a chemical polymerization initiator allows preparing a mixture of which the curing reaction proceeds smoothly even in the oral cavity at ordinary temperature and thus has been widely used in the field of dental materials.

However, curable compositions including benzoyl peroxide have the following problem: because the curable compositions containing benzoyl peroxide are often decomposed during storage at ordinary temperature to generate radicals due to the high polymerization activity of benzoyl peroxide; and therefore, the composition is cured during storage, or sufficient polymerization properties after long-term storage cannot be maintained because of the deactivation due to the decomposition.

As a curable composition containing a chemical polymerization initiator that solves the above-mentioned problems, those using a hydroperoxide compound that is thermodynamically stable as a peroxide have been proposed (Patent Literatures 2 and 3). This chemical polymerization type curable composition, which uses a thermally stable peroxide, is characterized by having excellent storage stability at ordinary temperature compared to the compositions using benzoyl peroxide. However, the activity thereof is low compared to the compositions using benzoyl peroxide and the like, and there is room for improvement in the curing time.

Patent Literatures 4 and 5 propose curable compositions containing a chemical polymerization initiator using a hydroperoxide compound as peroxide, a thiourea compound as a reducing agent, and a transition metal compound as an accelerator. These curable compositions have comparatively high stability to heat, and high storage stability at room temperature. On the other hand, these chemical polymerization initiator systems still have a lower polymerization reactivity and need a longer curing time as compared with the conventional chemical polymerization catalyst system composed of benzoyl peroxide/aromatic amine compound. Furthermore, the pot life after the storage of these curable composition changes greatly over time, and the mixture obtained by mixing the first pack and the second pack after storage tends to solidify, which are problematic.

Patent Literature 6 also proposes a chemical polymerization initiator substantially free of peroxide, which is composed of a Lewis acidic compound, a tertiary amine compound, and a sulfinic acid compound. A curable composition containing such a chemical polymerization initiator is substantially free of peroxide. Thus its storage stability is not affected by the chemical stability of the peroxide and the storage stability during storage at ordinary temperature is greatly improved. However, since the curable composition does not contain peroxide, its curing time is long, and there is room for improvement in its polymerization properties.

CITATION LIST

Patent Literature

Patent Literature 1: Japanese Patent No. 3449843
Patent Literature 2: Japanese Patent No. 5683337
Patent Literature 3: Japanese Patent No. 5846883
Patent Literature 4: Japanese Patent No. 5773557
Patent Literature 5: Japanese Patent Application Laid-Open No. 2009-144054
Patent Literature 6: Japanese Patent No. 4646264

SUMMARY OF INVENTION

Technical Problem

In order for the curable composition to exhibit the desired performance, it is desired that the curable composition have a polymerization property for reliable polymerization in the use environment of each material to provide a cured product.

Therefore, an object of the present invention is to provide a curable composition having sufficient polymerization properties even under acidic conditions.

Solution to Problem

As a result of intensive studies to solve the above-mentioned problem, the present inventors have found that a curable composition having the following configuration can solve the above problem, thereby completing the present invention.

The present invention includes the matters described in the following [1] to [19]

[1] A curable composition comprising (a) a polymerizable monomer having an acidic group, (b) a transition metal compound, (c) at least one compound selected from benzoxazole compounds and benzothiazole compounds, and (d) a reducing agent.

[2] The curable composition according to [1], in which the compound (c) does not include a compound having a mercapto group at the 2-position of a benzoxazole ring or a compound having a mercapto group at the 2-position of a benzothiazole ring.

[3] The curable composition according to [1] or [2], in which the reducing agent (d) comprises at least one compound selected from sulfinic acid, a salt of sulfinic acid, ascorbic acid, and a salt of ascorbic acid.

[4] The curable composition according to any one of [1] to [3], in which the compound (c) is at least one selected from benzoxazole, benzothiazole, and compounds represented by the following Formula (1),

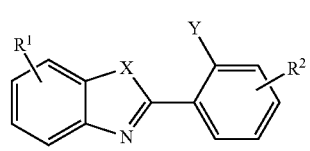

where X represents an oxygen atom or a sulfur atom, Y represents a hydroxyl group or an amino group, and $R^1$ and $R^2$ each independently represent a hydrogen atom, a halogen atom, or a hydrocarbon group having 1 to 4 carbon atoms.

[5] The curable composition according to any one of [1] to [4], in which the transition metal compound (b) is at least one selected from copper compounds and vanadium compounds.

[6] The curable composition according to any one of [1] to [5], further comprising (e) a polymerizable monomer having no acidic group.

[7] The curable composition according to any one of [1] to [6], wherein the curable composition is substantially free of (f) a peroxide.

[8] The curable composition according to any one of [1] to [6], further comprising (f) a peroxide.

[9] The curable composition according to [8], in which the peroxide (f) is at least one selected from hydroperoxide compounds and peroxyester compounds.

[10] The curable composition according to any one of [1] to [9], further comprising at least one selected from (g) a photopolymerization initiator, (h) a filler, (i) an organic solvent, and (j) water.

[11] The curable composition according to any one of [1] to [10], in which a total of the transition metal compound (b), the compound (c), and the reducing agent (d) is 0.1 to 40 parts by mass, based on 100 parts by mass of polymerizable monomers.

[12] The curable composition according to any one of [1] to [11], in which a content of the transition metal compound (b) is 0.001 to 5 parts by mass, based on 100 parts by mass of polymerizable monomers.

[13] The curable composition according to any one of [1] to [12], in which a content of the compound (c) is 0.1 to 20 parts by mass, based on 100 parts by mass of polymerizable monomers.

[14] The curable composition according to any one of [1] to [13], in which a content of the reducing agent (d) is 0.01 to 20 parts by mass, based on 100 parts by mass of polymerizable monomers.

[15] The curable composition according to any one of [1] to [14], wherein the curable composition is for dental use.

[16] A dental composition comprising the curable composition according to any one of [1] to [15], in which the dental composition is a dental adhesive resin cement, a dental composite resin, a dental bonding material, a dental backing material, a dental root filler, an orthodontic adhesive, a mobile tooth fixing material, a dental sealant, a temporary dental cement, or a dental filler material.

[17] A cured product of the curable composition according to any one of [1] to [15] or the dental composition according to [16].

[18] A kit for initiating polymerization comprising (A) a first pack and (B) a second pack, the first pack (A) containing (a) a polymerizable monomer having an acidic group and (b) a transition metal compound, the second pack (B) containing (c) at least one compound selected from benzoxazole compounds and benzothiazole compounds and (d) a reducing agent.

[19] A polymerization initiator comprising (c) at least one compound selected from benzoxazole compounds and benzothiazole compounds and (d) a reducing agent.

Advantageous Effects of Invention

The curable composition of the present invention has sufficient polymerization properties as a chemical polymerization type curable composition.

DESCRIPTION OF EMBODIMENTS

The present invention will now be described in detail. Herein, "(meth)acryl" means "acryl" or "methacryl", and for example, "(meth)acrylic acid" means acrylic acid or methacrylic acid. Similarly, "(meth)acryloyl" means "acryloyl" or "methacryloyl", and "(meth)acrylate" means "acrylate" or "methacrylate".

[Curable Composition]

A curable composition of the present invention comprises (a) a polymerizable monomer having an acidic group, (b) a transition metal compound, (c) at least one compound selected from benzoxazole compounds and benzothiazole compounds, and (d) a reducing agent, and, as necessary, at least one selected from the components (e) to (j) described below and other components.

The curable composition of the present invention has sufficient polymerization properties as a chemical polymerization type curable composition. Further, the curable composition of the present invention is capable of providing a cured product having a sufficient strength as a cured product for dental materials. Furthermore, according to the present invention, a dual cure type curable composition which uses a photopolymerization initiator in combination can also be provided.

In the present invention, all of the transition metal compound (b), the compound (c), and the reducing agent (d) or a partial combination of these acts as a so-called chemical polymerization initiator. Therefore, the curable composition of the present invention contains a chemical polymerization initiator.

The curable composition of the present invention may, in a mode, be composed of a single pack and contain all of the above-mentioned components in the pack, or may, in another mode, be separately packed in a plurality of packs, e.g. (A) a first pack and (B) a second pack (separately packed curable composition). The former mode or a mixture obtained from the latter mode by mixing a plurality of separate packs may also be specifically referred to as a "polymerizable mixture". In the present invention, a polymerizable mixture prepared by mixing the packs stored for a long period of time at ordinary temperature or higher can give a curable composition that maintains sufficient polymerization activity.

((a) Polymerizable Monomer Having an Acidic Group)

Because of the polymerizable monomer (a) having an acidic group in the curable composition, a curable composition of the present invention having excellent adhesion can be obtained.

Examples of the polymerizable monomer (a) having an acidic group include an acidic group-containing radical polymerizable monomer. A conventionally used polymerizable monomer can be used as a dental adhesive monomer.

Examples of a radical polymerizable unsaturated group included in the acidic group-containing radical polymerizable monomer include a (meth)acryloyl group, a (meth)acrylamide group, a styryl group, a vinyl group, and an allyl group.

Among these radically polymerizable unsaturated groups, in view of ease of removal of the polymerizable group by hydrolysis in the oral cavity, for example, a (meth)acryloyl group and a (meth)acrylamide group are preferred, a methacryloyl group and a (meth)acrylamide group are more preferred, and a methacryloyl group is still more preferred.

Examples of the acidic group included in the polymerizable monomer (a) having an acidic group include a carboxylic acid group, a carboxylic anhydride group, a phosphoric acid group, a thiophosphoric acid group, a pyrophosphoric acid group, a thiopyrophosphoric acid group, a phosphonic acid group, a thiophosphonic acid group, a sulfonic acid group. These acidic groups may be in the form of an acid chloride, an alkali metal salt, an alkaline earth metal salt, an ammonium salts, and the like.

Examples of the polymerizable monomer having a phosphoric acid group include (meth)acryloyloxy alkyl dihydrogen phosphates, such as 2-(meth)acryloyloxy ethyl dihydrogen phosphate, 3-(meth)acryloyloxy propyl dihydrogen phosphate, 4-(meth)acryloyloxy butyl dihydrogen phosphate, 5-(meth)acryloyloxy pentyl dihydrogen phosphate, 6-(meth)acryloyloxy hexyl dihydrogen phosphate, 7-(meth)acryloyloxy heptyl dihydrogen phosphate, 8-(meth)acryloyloxy octyl dihydrogen phosphate, 9-(meth)acryloyloxy nonyl dihydrogen phosphate, 10-(meth)acryloyloxy decyl dihydrogen phosphate, 11-(meth)acryloyloxy undecyl dihydrogen phosphate, 12-(meth)acryloyloxy dodecyl dihydrogen phosphate, 16-(meth)acryloyloxy hexadecyl dihydrogen phosphate, and 20-(meth)acryloyloxy icosyl dihydrogen phosphate, bis[(meth)acryloyloxyalkyl] hydrogen phosphates, such as bis[2-(meth)acryloyloxyethyl] hydrogen phosphate, bis[4-(meth)acryloyloxybutyl] hydrogen phosphate, bis[6-(meth)acryloyloxyhexyl] hydrogen phosphate, bis[8-(meth)acryloyloxyoctyl] hydrogen phosphate, bis[9-(meth)acryloyloxynonyl] hydrogen phosphate, and bis[10-(meth)acryloyloxydecyl] hydrogen phosphate, 1,3-di(meth)acryloyloxypropyl dihydrogen phosphate, 2-(meth)acryloyloxyethyl phenyl hydrogen phosphate, 2-(meth)acryloyloxyethyl-2-bromoethyl hydrogen phosphate, bis[2-(meth)acryloyloxy-(1-hydroxymethyl)ethyl] hydrogen phosphate, pentaacryloyl dipentaerythritol hydrogen phosphate, and acid chlorides, alkali metal salts, alkaline earth metal salts, and ammonium salts thereof. Further examples include compounds in which the phosphate acid group in these compounds is substituted with a thiophosphoric acid group.

Examples of the polymerizable monomer having a pyrophosphate acid group include bis[2-(meth)acryloyloxyethyl] pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate, bis[10-(meth)acryloyloxydecyl] pyrophosphate, and acid chlorides, alkali metal salts, alkaline earth metal salts, and ammonium salts thereof. Further examples include compounds in which the pyrophosphate acid group in these compounds is substituted with a thiopyrophosphoric acid group.

Examples of the polymerizable monomer having a phosphonic acid group include 2-(meth)acryloyloxyethyl phenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and acid chlorides, alkali metal salts, alkaline earth metal salts, and ammonium salts thereof. Further examples include compounds in which the phosphonic acid group in these compounds is substituted with a thiophosphonic acid group.

Examples of the polymerizable monomer having a sulfonic acid group include 2-sulfoethyl (meth)acrylate, 2-sulfo-1-propyl (meth)acrylate, 1-sulfo-2-propyl (meth)acrylate, 1-sulfo-2-butyl (meth)acrylate, 3-sulfo-2-butyl (meth)acrylate, 3-bromo-2-sulfo-2-propyl (meth)acrylate, 3-methoxy-1-sulfo-2-propyl (meth)acrylate, 1,1-dimethyl-2-sulfoethyl (meth)acrylamide, and acid chlorides, alkali metal salts, alkaline earth metal salts, and ammonium salts thereof.

Examples of the polymerizable monomer having a carboxylic acid group or a carboxylic acid anhydride group include monocarboxylic acids, dicarboxylic acids, tricarboxylic acids, and tetracarboxylic acids, or derivatives thereof. Examples of these include (meth)acrylic acid, maleic acid, p-vinylbenzoic acid, 11-(meth)acryloyloxy-1,1-undecanedicarboxylic acid (in the case of methacrylate: "MAC10"), 1,4-di(meth)acryloyloxy ethyl pyromellitic acid, 6-(meth)acryloyloxyethylnaphthalene-1,2,6-tricarboxylic acid, 4-(meth)acryloyloxymethyl trimellitic acid and anhydrides thereof, 4-(meth)acryloyloxyethyl trimellitic acid (in the case of methacrylate: "4-MET") and anhydrides thereof (in the case of methacrylate: 4-META), 4-(meth)acryloyloxybutyl trimellitic acid and anhydrides thereof, 4-[2-hydroxy- 3-(meth)acryloyloxy] butyl trimellitic acid and anhydrides thereof, 2,3-bis(3,4-dicarboxybenzoyloxy) propyl (meth) acrylate, N,O-di(meth)acryloyl tyrosine, 0-(meth)acryloyl tyrosine, N-(meth)acryloyl tyrosine, N-(meth)acryloylphenylalanine, N-(meth)acryloyl-p-aminobenzoic acid, N-(meth)acryloyl-O-aminobenzoic acid, N-(meth)acryloyl-5-aminosalicylic acid (in the case of methacrylate: "5-MASA"), N-(meth)acryloyl-4-aminosalicylic acid, 2 or 3 or 4-(meth)acryloyloxybenzoic acid, an addition product of 2-hydroxyethyl (meth)acrylate and pyromellitic acid dianhydride (in the case of methacrylate: "PMDM"), an addition reaction product of 2-hydroxyethyl (meth)acrylate and maleic anhydride or 3,3',4,4'-benzophenonetetracarboxylic dianhydride (in the case of methacrylate: "BTDA") or 3,3',4,4'-biphenyltetracarboxylic dianhydride, 2-(3,4-dicarboxybenzoyloxy)-1,3-di(meth)acryloyloxypropane, an adduct of N-phenylglycine or N-tolylglycine and glycidyl (meth)acrylate, 4-[(2-hydroxy-3-(meth)acryloyloxypropyl) amino] phthalic acid, 3 or 4-[N-methyl-N-(2-hydroxy-3-(meth)acryloyloxypropyl)amino] phthalic acid, and acid chlorides, alkali metal salts, alkaline earth metal salts, and ammonium salts thereof.

Among the polymerizable monomers (a) having an acidic group, 4-methacryloyloxyethyl trimellitic acid, 4-methacryloyloxyethyl trimellitic anhydride, and 10-methacryloyloxydecyldihydrogen phosphate are preferred in view of adhesion to teeth.

These compound as the polymerizable monomer (a) having an acidic group may be used singly or in combination of two or more thereof.

The content of the polymerizable monomer (a) having an acidic group in the curable composition of the present invention is preferably 1 to 50 parts by mass, more preferably 3 to 35 parts by mass, and still more preferably 5 to 25 parts by mass based on 100 parts by mass of a total of polymerizable monomers. In such a mode, the polymerizable mixture tends to have excellent polymerization properties, and the cured product thus obtained tends to have excellent adhesive strength and mechanical properties.

Examples of the polymerizable monomer include the polymerizable monomer (a) having an acidic group and (e) a polymerizable monomer having no acidic group described later.

The content of each component is described herein; however, in the case of the separately packed curable composition to be described later, the total amount of a component obtained by summing up the amount of the component in the plurality of separate packs may be within the range described herein.

((b) Transition Metal Compound)

Because of including the transition metal compound (b) in the curable composition, sufficient polymerization properties can be imparted to the curable composition of the present invention. Examples of the transition metal compound (b) include copper compounds, vanadium compounds, cobalt compounds, and nickel compounds, iron compounds, and molybdenum compounds.

Examples of the copper compound include monovalent to divalent copper compounds, such as copper acetylacetonate, copper oleate, copper acetate, copper gluconate, copper citrate, copper phthalate, copper naphthenate, copper hydroxide, copper methoxide, copper ethoxide, copper isopropoxide, copper chloride, and copper bromide.

The vanadium compound is preferably at least one compound selected from trivalent to pentavalent vanadium compounds, such as vanadium(III) acetylacetonate, vanadium (III) naphthenate, vanadyl stearate, vanadium benzoylacetonate, bis(maltolate) oxovanadium(IV), oxobis(1-phenyl-1,3-butanedionate) vanadium(IV), vanadyl(IV) acetylacetonate, divanadium(IV) tetroxide, vanadyl(IV) oxalate, vanadyl(IV) sulfate, oxobis(1-phenyl-1,3-butanedionate) vanadium(IV), bis(maltolate) oxovanadium(IV), vanadium (V) oxytriisopropoxide, vanadium(V) pentoxide, sodium metavanadate(V), ammonium metavanadate (V).

Examples of the cobalt compound include cobalt acetylacetonate, cobalt acetate, cobalt naphthenate, cobalt oleate, cobalt stearate, cobalt 2-ethylhexanoate, cobalt benzoate, cobalt oxalate, cobalt citrate, cobalt carbonate, cobalt nitrate, cobalt sulfate, cobalt phosphate, cobalt perchlorate, cobalt thiocyanate, cobalt oxide, cobalt sulfide, cobalt fluoride, cobalt chloride, cobalt bromide, cobalt hydroxide, and cobalt isopropoxide.

Examples of the nickel compound include nickel acetylacetonate, bis(dithiobenzyl)nickel, bis(cyclopentadienyl) nickel, nickel formate acetate, nickel acetate, nickel lactate, nickel naphthenate, nickel 2-ethylhexanoate, nickel oxalate, nickel citrate, nickel stearate, nickel perchlorate, nickel oxide, nickel sulfide, nickel fluoride, nickel chloride, nickel bromide, nickel iodide, nickel carbonate, nickel nitrate, nickel sulfate, nickel hydroxide, and nickel ethoxide.

Examples of the iron compound include iron acetylacetonate, ferrocene, iron acetate, iron stearate, iron 2-ethylhexanoate, iron oxalate, iron citrate, iron gluconate, iron nitrate, iron sulfate, iron phosphate, iron perchlorate, iron oxide, iron sulfide, iron fluoride, iron chloride, iron bromide, potassium hexacyanoferrate, and iron ethoxide.

Examples of the molybdenum compound include molybdenum oxide, molybdenum oxide acetylacetonate, molybdenum ethoxide, bis(2,4-pentadionato) molybdenum oxide, and molybdenyl diethyldithiocarbamate.

Among the transition metal compounds (b), in view of excellent polymerization properties of the polymerizable mixture and stability during storage, it is preferable to use at least one selected from copper compounds and vanadium compounds. Moreover, in view of solubility in a polymerizable monomer and handling, monovalent or divalent copper chloride, copper bromide, copper acetate, vanadium(III) acetylacetonate and vanadyl(IV) acetylacetonate are preferred.

These compounds as the transition metal compound (b) may be used singly or in combination of two or more thereof.

The content of the transition metal compound (b) in the curable composition of the present invention is preferably 0.001 to 5 parts by mass, more preferably 0.005 to 3 parts by mass, and still more preferably 0.01 to 1 part by mass, based on 100 parts by mass of the polymerizable monomer. If the content of the transition metal compound (b) is less than this lower limit, the effects brought about by the inclusion of the transition metal compound (b) may not be obtained, and if the content is more than this upper limit, the polymerizable monomer included in the first pack (A) to be described later tends to be more easily polymerized during storage.

((c) At Least One Compound Selected from Benzoxazole Compounds and Benzothiazole Compounds)

The curable composition of the present invention contains at least one compound (c) selected from benzoxazole compounds and benzothiazole compounds. The compound (c) has an effect of increasing the polymerization catalyst activity of the transition metal compound (b). By blending the compound (c) in the curable composition of the present invention, the polymerization property of the polymerizable mixture improves. Furthermore, a cured product having a good mechanical strength can be obtained, and discoloration of the cured product is less likely to occur, whereby an aesthetically good cured product can be obtained. This is probably because the at least one compound (c) selected from benzoxazole compounds and benzothiazole compounds functions as a ligand for the transition metal compound (b) and thus improves the polymerization property.

In one embodiment, when a compound that can also be classified as the compound (c) among the reducing agents (d) is used as the reducing agent (d), at least one selected from benzoxazole compounds and benzothiazole compounds other than that compound can be used as the compound (c). Further, in one embodiment, when a compound that can also be classified as the reducing agent (d) among the compounds (c) is used as the compound (c), a reducing agent (d) other than that compound can be selected and used.

Further, compounds having a mercapto group at the 2-position of a benzoxazole ring and compounds having a mercapto group at the 2-position of a benzothiazole ring have reactivity derived from thiol, so that there is a possibility that a reaction product between the polymerizable monomer in the curable composition and a thiol occurs. Therefore, it is preferable to exclude compounds having a mercapto group at the 2-position of a benzoxazole ring and compounds having a mercapto group at the 2-position of a benzothiazole ring from the compound (c).

However, in one embodiment, the curable composition of the present invention may include a compound having a mercapto group at the 2-position of the benzoxazole ring or a compound having a mercapto group at the 2-position of the benzothiazole ring as the compound (c).

As long as the compound (c) has a benzoxazole ring and/or a benzothiazole ring, the compound (c) may be unsubstituted or have any functional group and any known compound can be used as the compound (c) without limitation.

Examples of the compound (c) include benzoxazole, 2-methylbenzoxazole, 2-phenylbenzoxazole, 2-(2-benzoxazolyl)acetic acid, 2-(2-benzoxazolyl)maleic acid, 7-aminobenzoxazole, benzoxazole 4-carboxylic acid, benzoxazole 7-carboxylic acid, 2-(2-hydroxyphenyl)benzoxazole, 2-(2-aminophenyl)benzoxazole, benzothiazole, 2-methylbenzothiazole, 2-phenylbenzothiazole, 2-(2-benzothiazolyl)acetic acid, 2-(2-benzothiazolyl)maleic acid, 7-aminobenzothiazole, benzothiazole 4-carboxylic acid, benzothiazole 7-carboxylic acid, 2-(2-hydroxyphenyl)benzothiazole, and 2-(2-aminophenyl)benzothiazole.

The compound (c) is preferably a compound represented by the following Formula (1).

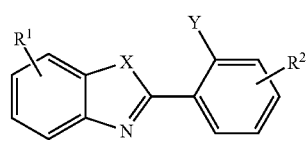

(1)

In Formula (1), X represents an oxygen atom or a sulfur atom, and Y represents a hydroxyl group or an amino group. $R^1$ and $R^2$ each independently represent a hydrogen atom, a halogen atom, or a hydrocarbon group having 1 to 4 carbon atoms.

Examples of the halogen atom include a fluorine atom, a chlorine atom, a bromine atom, and an iodine atom.

Examples of the hydrocarbon group having 1 to 4 carbon atoms include alkyl groups such as a methyl group, an ethyl group, a n-propyl group, an isopropyl group, a n-butyl group, an isobutyl group, and a tert-butyl group.

Specific examples of the compound represented by Formula (1) include 2-(2-hydroxyphenyl)benzoxazole, 2-(2-aminophenyl)benzoxazole, 2-(2-hydroxyphenyl)benzothiazole, and 2-(2-aminophenyl)benzothiazole.

Among the compounds (c), in view of polymerization properties and storage stability of the composition, benzoxazole, benzothiazole, and compounds represented by Formula (1) are preferred, and benzoxazole, 2-(2-hydroxyphenyl)benzoxazole, benzothiazole, and 2-(2-hydroxyphenyl)benzothiazole are more preferred.

These compounds as the compound (c) may be used singly or in combination of two or more thereof.

The content of the compound (c) in the curable composition of the present invention is preferably 0.1 to 20 parts by mass, more preferably 0.5 to 10 parts by mass, and still more preferably 1 to 5 parts by mass, based on 100 parts by mass of the polymerizable monomer. If the content of the compound (c) is less than the lower limit, the effect of improving the polymerization properties sufficient for the curable composition of the present invention may not be obtained.

((d) Reducing Agent)

Examples of the reducing agent (d) used in the present invention include a sulfur-based reducing agent, a boron-based reducing agent, ascorbic acid or a salt thereof, aldehydes, oxalic acid or a salt thereof, and an aromatic amine compound.

Examples of the sulfur-based reducing agent include sulfinic acid or salts thereof, sulfites such as sodium sulfite, hydrogen sulfites such as sodium hydrogen sulfite, pyrosulfites such as sodium pyrosulfite, and thiosulfates such as sodium thiosulfate.

Examples of the boron-based reducing agent include aryl borate compounds such as tetraalkylboron, trialkylphenylboron, dialkyldiphenylboron, monoalkyltriphenylboron, and tetraphenylboron, and salts thereof.

Examples of the aldehydes include terephthalaldehyde and benzaldehyde derivatives.

Among these, at least one selected from sulfinic acid, a salt of sulfinic acid, ascorbic acid, and a salt of ascorbic acid is preferable in view of enabling the polymerization properties to improve.

Examples of the salt include alkali metal salts such as sodium salts, potassium salts, and lithium salts, alkaline earth metal salts such as magnesium salts, calcium salts, and barium salts, amine salts, ammonium salts, and pyridinium salts.

Further, the aromatic amine compound brings an excellent polymerization promotion effect when blended in the curable composition as the reducing agent. However, when an aromatic amine compound is used together with the polymerizable monomer (a) having an acidic group, the aromatic amine compound may be deactivated by neutralization, thereby losing its polymerization promotion effects. The curable composition of the present invention can exhibit sufficient polymerization properties even in such a mode, but it is preferable to use a reducing agent other than the aromatic amine compound taking the deactivation into consideration.

Further, sulfinic acid or a salt thereof is particularly preferable because sulfinic acid or a salt thereof improves polymerization properties and suppresses discoloration or the like thereby improving aesthetics, which is suitable for dental use. The sulfinic acid or salt thereof will be described in detail below.

<<(d1) At Least One Compound Selected from Sulfinic Acid and a Salt Thereof>>

Because of including at least one compound (d1) selected from sulfinic acid and a salt thereof in the curable composition, the effect of improving polymerization properties of the curable composition of the present invention can be obtained.

Examples of the at least one compound (d1) selected from sulfinic acid and a salt thereof include: alkanesulfinic acids such as methanesulfinic acid, ethanesulfinic acid, propanesulfinic acid, hexanesulfinic acid, octanessulfinic acid, decanesulfinic acid, and dodecanesulfinic acid; cycloaliphatic sulfinic acids such as cyclohexanesulfinic acid and cyclooctanesulfinic acid; aromatic sulfinic acids such as benzenesulfinic acid, o-toluenesulfinic acid, p-toluenesulfinic acid, ethylbenzenesulfinic acid, decylbenzenesulfinic acid, dodecylbenzenesulfinic acid, 2,4,6-trimethylbenzenesulfinic acid, 2,4,6-triethylbenzenesulfinic acid, 2,4,6-triisopropylbenzenesulfinic acid, and naphthalenesulfinic acid; and salts of those sulfinic acids, such as a sodium salt, a potassium salt, a lithium salt, and other alkali metal salts thereof, a magnesium salt, a calcium salt, a barium salt, and other alkaline earth metal salts, amine salts, ammonium salts, and pyridinium salts thereof. Among these, aromatic sulfinic acids and salts thereof are preferred, in view of the storage stability in the curable composition and the polymerization activity of the polymerizable mixture.

These compounds as the reducing agent (d) may be used singly or in combination of two or more thereof.

The content of the reducing agent (d) in the curable composition of the present invention is preferably 0.01 to 20 parts by mass, more preferably 0.1 to 10 parts by mass, and still more preferably 1 to 5 parts by mass, based on 100 parts by mass of the polymerizable monomer. In such a mode, the curing time of the polymerizable mixture, the polymerization properties in consideration of the pot life, and the adhesive strength of the obtained cured product tend to be excellent. In particular, when the reducing agent (d) is at least one compound (d1) selected from sulfinic acid and a salt thereof, the content is preferably as described above.

Further, the total of the transition metal compound (b), the compound (c), and the reducing agent (d) in the curable composition of the present invention is preferably 0.1 to 40 parts by mass, more preferably 0.5 to 23 parts by mass, and still more preferably 1 to 10 parts by mass, based on 100 parts by mass of the polymerizable monomer. In such a mode, the polymerization properties and storage stability of the curable composition and the mechanical strength of the cured product provided by the curable composition tend to be excellent.

((e) Polymerizable Monomer Having No Acidic Group)

Because of including the polymerizable monomer (e) having no acidic group in the curable composition, various physical properties of the obtained cured product, such as mechanical strength and adhesive strength, can be improved. Moreover, because of including the polymerizable monomer (e) having no acidic group in the curable composition, the fluidity of the curable composition of the present invention can be improved.

Examples of the polymerizable monomer (e) having no acidic group include a radical polymerizable monomer having no acidic group. Examples of a radical polymerizable unsaturated group included in the radical polymerizable monomer having no acidic group include a (meth)acryloyl group, a (meth)acrylamide group, a styryl group, a vinyl group, and an allyl group. Among these radically polymerizable unsaturated groups, in view of ease of removal of the polymerizable group by hydrolysis in the oral cavity, for example, a (meth)acryloyl group and a (meth)acrylamide group are preferred, a methacryloyl group and a (meth)acrylamide group are more preferred, and a methacryloyl group is still more preferred.

Examples of the radical polymerizable monomer having no acidic group include:

monofunctional monomers, such as hydroxyalkyl (meth)acrylates, such as 2-hydroxyethyl (meth)acrylate, 3-hydroxypropyl (meth)acrylate, 4-hydroxybutyl (meth)acrylate, 6-hydroxyhexyl (meth)acrylate, and 10-hydroxydecyl (meth)acrylate, 2-(dimethylamino)ethyl (meth)acrylate, N-methyl-N-phenylaminoethyl (meth)acrylate, N-ethyl-N-phenylaminoethyl (meth)acrylate, propylene glycol mono (meth)acrylate, glycerol mono(meth)acrylate, erythritol mono(meth)acrylate, N-methylol (meth)acrylamide, N-hydroxyethyl (meth)acrylamide, N,N-(dihydroxyethyl) (meth)acrylamide, methyl (meth)acrylate, ethyl (meth)acrylate, propyl (meth)acrylate, isopropyl (meth)acrylate, butyl (meth)acrylate, isobutyl (meth)acrylate, benzyl (meth)acrylate, lauryl (meth)acrylate, 2,3-dibromopropyl (meth)acrylate, 3-(meth)acryloyloxypropyltrimethoxysilane, 11-(meth)acryloyloxyundecyltrimethoxysilane, (meth)acrylamide, dimethylaminoethyl (meth)acrylate, dimethylaminopropyl (meth)acrylate, dimethylaminobutyl (meth)acrylate, (meth)acryloyloxy dodecylpyridinium bromide, (meth)acryloyloxy dodecylpyridinium chloride, and (meth)acryloyloxy hexadecylpyridinium chloride;

bifunctional monomers having an aromatic ring, such as 2,2-bis((meth)acryloyloxyphenyl) propane, 2,2-bis[4-(3-(meth)acryloyloxy-2-hydroxypropoxy)phenyl] propane (commonly referred to as "Bis-GMA"), 2,2-bis(4-(meth)acryloyloxyphenyl) propane, 2,2-bis(4-(meth)acryloyloxypolyethoxyphenyl) propane, 2,2-bis(4-(meth)acryloyloxydiethoxy)phenyl) propane), 2,2-bis(4-(meth)acryloyloxytetraethoxyphenyl) propane, 2,2-bis(4-(meth)acryloyloxypentaethoxyphenyl) propane, 2,2-bis(4-(meth)acryloyloxydipropoxyphenyl) propane, 2-(4-(meth)acryloyloxyethoxyphenyl)-2-(4-(meth)acryloyloxydiethoxyphenyl) propane, 2-(4-(meth)acryloyloxydiethoxyphenyl)-2-(4-(meth)acryloyloxytriethoxyphenyl) propane, 2-(4-(meth)acryloyloxydipropoxyphenyl)-2-(4-(meth)acryloyloxytriethoxyphenyl) propane, 2,2-bis(4-(meth)acryloyloxypropoxyphenyl) propane, 2,2-bis(4-(meth)acryloyloxyiso- propoxyphenyl) propane, and 1,4-bis(2-(meth)acryloyloxyethyl) pyromellitate;

bifunctional monomers having an aliphatic carbon chain, such as alkylene glycol di(meth)acrylates such as glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, and neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,12-dodecanediol di(meth)acrylate, 1,2-bis(3-(meth)acryloyloxy-2-hydroxypropoxy) ethane, 1,6-bis(methacryloxyethyloxycarbonylamino)-2,2,4-trimethylhexane (commonly referred to as "UDMA"), and 1,2-bis(3-(meth)acryloyloxy-2-hydroxypropoxy) ethane;

trifunctional or higher polyfunctional monomers, such as trimethylolpropane tri(meth)acrylate, trimethylolethane tri(meth)acrylate, trimethylolmethane tri(meth)acrylate, tris(2-

(meth)acryloxyethyl) isocyanurate, pentaerythritol tri(meth) acrylate, pentaerythritol tetra(meth)acrylate, dipentaerythritol penta(meth)acrylate, N,N-(2,2,4-trimethylhexamethylene) bis[2-(aminocarboxy)propane-1,3-diol]tetramethacrylate, and 1,7-diacryloyloxy-2,2,6,6-tetraacryloyloxymethyl-4-oxyheptane;

polymerizable monomers synthesized by an addition reaction of a compound having an isocyanate group (—NCO), such as hexamethylene diisocyanate (HDI), tolylene diisocyanate (TDI), xylylene diisocyanate (XDI), diphenylmethane diisocyanate (MDI), isophorone diisocyanate (IPDI), and trimethylhexamethylene diisocyanate (TMHMDI) with a (meth)acrylate compound having a hydroxyl group (—OH) (e.g., described in International Publication No. 2012/157566, International Publication No. 2015/015220, International Publication No. 2015/015221, and Japanese Patent Application Laid-open No. 2016-094482), such as 2-hydroxyethyl (meth)acrylate, 2-hydroxypropyl (meth)acrylate, 2-hydroxybutyl (meth)acrylate, 6-hydroxyhexyl (meth)acrylate, 10-hydroxydecyl (meth) acrylate, 3-chloro-2-hydroxypropyl (meth)acrylate, 2-hydroxy-3-phenoxypropyl (meth)acrylate, glycerin mono (meth)acrylate, N-hydroxyethyl (meth)acrylamide, N,N-(dihydroxyethyl) (meth)acrylamide, bisphenol A diglycidyl (meth)acrylate, 2-hydroxy-3-acryloyloxypropyl (meth)acrylate, 2,2-bis[4-[3-(meth)acryloyloxy-2-hydroxypropoxy]phenyl]propane, 1,2-bis[3-(meth)acryloyloxy-2-hydroxypropoxy] ethane, pentaerythritol tri (meth)acrylate, and dipentaerythril tri- or tetra-(meth)acrylate.

Among the radical polymerizable monomers (e) having no acidic group, 1,6-bis(methacryloxyethyloxycarbonylamino)-2,2,4-trimethylhexane (UDMA), bisphenol A diglycidyl methacrylate (Bis-GMA), and 2,2-bis (4-methacryloyloxypolyethoxyphenyl) propane, a compound having an average addition mole number of ethoxy groups of 2.6 (commonly referred to as "D-2.6E"), 2-hydroxyethyl methacrylate (HEMA), glycerol dimethacrylate (GDMA), and triethylene glycol dimethacrylate (TEGDMA) are preferred in view of physical properties and ease of handling.

These compounds as the polymerizable monomer (e) having no acidic group may be used singly or in combination of two or more thereof.

The content of the polymerizable monomer (e) having no acidic group in the curable composition of the present invention is preferably 50 to 99 parts by mass, more preferably 65 to 97 parts by mass, and still more preferably 75 to 95 parts by mass based on 100 parts by mass of a total of the polymerizable monomer. In such a mode, the fluidity of the curable composition can be improved, and the mechanical strength and adhesive strength of the cured product obtained from the polymerizable mixture can be improved.

((f) Peroxide)

Although the curable composition of the present invention may be substantially free of (f) a peroxide, the curable composition may contain the peroxide (f) depending on the embodiment. When the curable composition contains the peroxide (f), the polymerization properties of the polymerizable mixture tends to improve, and the cured product thus obtained tends to have excellent mechanical strength and adhesive strength.

As the peroxide (f), any known compound may be used without any limitation, including diacyl peroxide compounds such as benzoyl peroxide, peroxyester compounds such as t-butyl peroxybenzoate, alkyl peroxides such as 1,1-di(t-butylperoxy)cyclohexane, hydroperoxide compounds such as 1,1,3,3-tetramethylbutyl hydroperoxide, and inorganic peroxides such as persulfate. Peroxyester compounds and hydroperoxide compounds are particularly preferred because of the excellent effect obtained when being blended in the curable composition of the present invention. In the case of using a vanadium compound as the transition metal compound (b), it is particularly preferable to use a hydroperoxide compound.

The peroxyester compound is not particularly limited, and any known peroxyester compound may be used as long as it has an acyl group on one side of the peroxy groups (—OO— group) and a hydrocarbon group (or an organic group similar thereto) on the other side of the peroxy group. Specific examples thereof include t-butyl peroxyisobutyrate, t-butyl peroxylaurate, t-butyl peroxy-2-ethylhexyl monocarbonate, t-butyl peroxyisononanoate, t-butyl peroxyacetate, t-butyl peroxybenzoate, t-butylperoxy-3,5,5-trimethylhexanoate, 2,5-dimethyl-2,5-bis(2-ethylhexanoylperoxy)hexane, cumylperoxyneodecanoate, 1,1,3,3-tetramethylbutylperoxyneodecanoate, 2,5-dimethyl-2,5-bis(m-toluoylperoxy)hexane, and 2,5-dimethyl-2,5-bis(benzoylperoxy) hexane. Among these, t-butyl peroxybenzoate and t-butyl peroxyisononanoate are preferable in view of storage stability and polymerization activity.

The hydroperoxide compound is not particularly limited, and any known hydroperoxide compound may be used as long as it has a hydrocarbon group (or an organic group similar thereto) on one side of the peroxy groups (—OO— group) and hydrogen on the other side of the peroxy group. Specific examples thereof include p-menthane hydroperoxide, diisopropylbenzene hydroperoxide, 1,1,3,3-tetramethylbutyl hydroperoxide, cumene hydroperoxide, t-hexyl hydroperoxide, and t-amyl hydroperoxide. Among these, 1,1,3,3-tetramethylbutyl hydroperoxide and cumene hydroperoxide are preferable in view of storage stability and polymerization activity.

The compounds as the peroxide (f) may be used singly or in combination of two or more thereof.

When the peroxide (f) is blended in the curable composition of the present invention, it is preferable to blend the peroxide (f) within a range that does not adversely affect the curing time of the polymerizable mixture, the pot life, and the color tone stability of the cured product thus obtained. The content of the peroxide (f) in the curable composition of the present invention is preferably 0.01 to 5 parts by mass, more preferably 0.05 to 3 parts by mass, and still more preferably 0.1 to 1 part by mass based on 100 parts by mass of the polymerizable monomer.

In some embodiments, the curable composition of the present invention may be substantially free of peroxide (f). The fact that the curable composition of the present invention is substantially free of peroxide (f) means that the content of the peroxide (f) in the curable composition of the present invention is less than 0.01 parts by mass based on 100 parts by mass of the polymerizable monomer.

((g) Photopolymerization Initiator)

In a preferred mode, the curable composition of the present invention contains a photopolymerization initiator (g). By blending the photopolymerization initiator (g) in the curable composition of the present invention, a dual cure type curable composition can be provided, thereby allowing curing of the composition by light irradiation.

As the photopolymerization initiator (g), any known photopolymerization initiator can be used without limitation. Examples thereof include an α-diketone/reducing agent, a ketal/reducing agent, a thioxanthone/reducing agent, and an acylphosphine oxide compound. The α-diketone/reducing agent means a combination of an α-diketone and a reducing agent, and the same applies to other examples. The "reducing agent" in the α-diketone/reducing agent means a reducing agent in the photopolymerization initiator (g), and does not include the above-described reducing agent (d) used as a reducing agent in the chemical polymerization initiator. The same applies to other examples.

When the photopolymerization initiator (g) is an α-diketone/aromatic amine compound, it is still more preferable that the aromatic amine compound contain an aromatic amine compound in which at least one of the hydrogen atoms bonded to the aromatic ring is substituted with an electron withdrawing group (including a halogen group).

Examples of the α-diketone include diacetyl, 2,3-pentadione, 2,3-hexadione, benzyl, 4,4'-dimethoxybenzyl, 4,4'-diethoxybenzyl, 4,4'-oxybenzyl, 4,4'-dichlorobenzyl, 4-nitrobenzyl, α-naphthyl, β-naphthyl, camphorquinone (CQ), camphorquinonesulfonic acid, camphorquinonecarboxylic acid, 1,2-cyclohexanedione, methylglyoxal, phenylglyoxal, pyruvic acid, benzoylformic acid, phenylpyruvic acid, methyl pyruvate, ethyl benzoylformate, methyl phenylpyruvate, butyl phenylpyruvate.

Examples of the ketal include benzyl dimethyl ketal, benzyl diethyl ketal.

Examples of the thioxanthone include 2-chlorothioxanthone, 2,4-diethylthioxanthone, 2-hydroxy-3-(9-oxy-9H-thioxanthen-4-yloxy)-N,N,N-trimethyl-propanaminium chloride, 2-hydroxy-3-(l-methyl-9-oxy-9H-thioxanthen-4-yloxy)-N,N,N-trimethyl-propaneaminium chloride, 2-hydroxy-3-(9-oxo-9H-thioxanthen-2-yloxy)-N,N,N-trimethyl-propanaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, 2-hydroxy-3-(1,3,4-trimethyl-9-oxo-9H-thioxanthen-2-yloxy)-N,N,N-trimethyl-1-propaneaminium chloride.

Examples of the acylphosphine oxide compound include benzoyldimethoxyphosphine oxide, benzoylethoxyphenylphosphine oxide, benzoyldiphenylphosphine oxide, 2-methylbenzoyldiphenylphosphine oxide, 2,4,6-trimethylbenzoyldiphenylphosphine oxide, bis(2,6-dimethoxybenzoyl)-2,4,4-trimethylpentylphosphine oxide, bis(2,4,6-trimethylbenzoyl)-phenylphosphine oxide.

Examples of the reducing agent include: peroxides such as hydrogen peroxide, Michler's ketone;

aldehydes such as citronellal, lauryl aldehyde, phthaldialdehyde, dimethylaminobenzaldehyde, and terephthalaldehyde;

mercaptans such as decanethiol, 3-mercaptopropyltrimethoxysilane, 4-mercaptoacetophenone, thiosalicylic acid, thiobenzoic acid; and aromatic amine compounds in which at least one of the hydrogen atoms bonded to the aromatic ring is substituted with an electron withdrawing group (including halogen atoms) such as N,N-dimethylaminobenzoic acid and alkyl esters thereof, such as methyl N,N-dimethylaminobenzoate, ethyl N,N-dimethylaminobenzoate (DMABAE), and butoxyethyl N,N-dimethylaminobenzoate (DMABABE), N,N-diethylaminobenzoic acid (DEABA) and alkyl esters thereof, N,N-dimethylaminobenzaldehyde (DMABAd), N,N-dimethylaminobenzophenone, and N,N-dimethyl-p-fluoroaniline.

Among the above-described examples of the photopolymerization initiator (g), a photopolymerization initiator containing a camphorquinone and/or an acylphosphine oxide compound is preferred, and in particular, a photopolymerization initiator containing camphorquinone having an absorption wavelength at 468 nm is more preferred in view of having an absorption wavelength in the visible light region and being polymerizable by visible light.

Examples of the photopolymerization initiator containing camphorquinone/reducing agent include a polymerization initiator containing camphorquinone/aromatic amine compound, a photopolymerization initiator containing camphorquinone/peroxide such as hydroperoxide, a polymerization initiator containing camphorquinone/aldehyde, and a polymerization initiator containing camphorquinone/mercaptan. Among these, a polymerization initiator containing a camphorquinone/aromatic amine compound is preferable. As the aromatic amine compound to be used, DMABAE and DMABABE are preferable in view of polymerization promotion effect in photopolymerization and handling.

These initiators as the photopolymerization initiator (g) may be used singly or in combination of two or more thereof.

The content of the photopolymerization initiator (g) in the curable composition of the present invention is preferably 0.001 to 5 parts by mass, more preferably 0.005 to 2 parts by mass, and still more preferably 0.01 to 1 part by mass based on 100 parts by mass of the polymerizable monomer. If the content of the photopolymerization initiator (g) is less than this lower limit, the curing of the curable composition by light irradiation may not proceed sufficiently. If the content is more than this upper limit, the polymerizable mixture may develop a color tone derived from the photopolymerization initiator (g), or the composition may be cured during storage.

((h) Filler)

The curable composition of the present invention may contain a filler (h). By including the filler (h) in the curable composition, it is possible, for example, to adjust the fluidity and consistency, the color tone, and the curability of the curable composition, to impart radiodensity, and to improve the mechanical strength of the obtained cured product. As the filler (h), any known fillers that are generally used may be used without limitation.

The filler (h) is generally broadly classified into an organic filler and an inorganic filler.

Examples of the organic filler include a powdered polymer filler obtained by pulverization of a polymer or by dispersion polymerization of a polymerizable monomer, and a filler obtained by polymerizing a polymerizable monomer with a crosslinking agent and then pulverizing the resulting polymer. Examples of the organic filler include a fine powder of a homopolymer or copolymer of a polymerizable monomer, such as polymethyl methacrylate (PMMA), polyethyl methacrylate, polypropyl methacrylate, polybutyl methacrylate (PBMA), polyvinyl acetate (PVAc), polyethylene glycol (PEG), polypropylene glycol (PPG), polyvinyl alcohol (PVA), polyurethane, polyurea, methyl methacrylate-ethyl methacrylate copolymer, crosslinked polymethyl methacrylate, crosslinked polyethyl methacrylate, ethylene-vinyl acetate copolymer, and styrene-butadiene copolymer. Further, the organic filler may also be a product obtained by adding a component such as a known pigment, a biologically active component, a polymerization initiator, and the like during the preparation of the organic filler.

Examples of the inorganic filler include a fine powder of various glasses (mainly composed of silicon dioxide, containing oxides such as heavy metals, boron and aluminum as necessary), various ceramics, diatomaceous earth, kaolin, clay mineral (montmorillonite, etc.), activated clay, synthetic zeolite, mica, calcium fluoride, ytterbium fluoride, calcium carbonate, calcium phosphate, aluminum sulfate, barium sulfate, calcium sulfate, zirconium dioxide, titanium dioxide, aluminum oxide, boron oxide, barium oxide, lanthanum oxide, strontium oxide, zinc oxide, calcium oxide, lithium oxide, sodium oxide, bismuth oxide, yttrium oxide, calcium phosphate, hydroxyapatite, aluminum hydroxide, sodium fluoride, potassium fluoride, sodium monofluorophosphate, lithium fluoride, ytterbium fluoride, and the like. Specific examples of such inorganic fillers include, for example, a fine powder of barium borosilicate glass (such as Kimble RAY-SORB T3000, Schott 8235, Schott GM27884, Schott G018-053, and Schott GM39923), a fine powder of strontium boroaluminosilicate glass (such as RAY-SORB T4000, Schott G018-093, Schott G018-163, and Schott GM32087), a fine powder of lanthanum glass (such as Schott GM31684), a fine powder of fluoroaluminosilicate glass (such as Schott G018-091 and Schott G018-117), and a fine powder of boroaluminosilicate glasses containing zirconium and/or cesium (such as Schott G018-307, G018-308 and G018-310).

It is also possible to use an organic-inorganic composite filler obtained by: adding a polymerizable monomer to the above-mentioned inorganic fillers in advance to form a paste, then polymerizing and curing, and grinding the resultant product. Examples of the organic-inorganic composite filler include a filler (TMPT•f) obtained by, from among the inorganic fillers, polymerizing and coating fine powder silica or zirconium oxide with a polymerizable monomer having trimethylolpropane tri(meth)acrylate (TMPT) as a main component, and then pulverizing the obtained polymer.

Further, one preferred mode of the dental composite resin is a dental composition incorporating a microfiller having a particle size of 0.1 µm or less. Preferred materials for fillers having such a small particle size include silica (e.g., AEROSIL (trade name)), alumina, zirconia and titania. Incorporating an inorganic filler having such a small particle size is advantageous in imparting a polishing smoothness and abrasion resistance to the cured product.

These fillers are subjected to surface treatment with a silane coupling agent or the like according to the purpose. When using an inorganic filler or an organic-inorganic composite filler, it is preferred to treat the filler surface with a known surface treating agent to improve the affinity and dispersibility with the polymerizable monomer used in the present invention. As such a surface treatment agent, a known silane coupling agent can be used without limitation. For example, γ-methacryloxyalkyltrimethoxysilane (number of carbons between methacryloxy group and silicon atom: 3 to 12), γ-methacryloxyalkyltriethoxysilane (number of carbons between methacryloxy group and silicon atom): 3 to 12), or an organosilicon compound such as vinyltrimethoxysilane, vinylethoxysilane, and vinyltriacetoxysilane is used. The concentration of the surface treatment agent is usually 0.1 to 20 parts by mass, and preferably 0.5 to 10 parts by mass, based on 100 parts by mass of the filler. In addition to the silane coupling agent, a surface treatment may be performed with a titanate coupling agent, an aluminate coupling agent, a zirco-aluminate coupling agent, or the like. Furthermore, the radical polymerizable monomer may be graft-polymerized onto the surface of the filler particles. As the surface treatment method, a known method can be used without particular limitation.

These fillers (h) can be appropriately added according to the application of the curable composition of the present invention. The fillers as the filler (h) may be used singly or in combination of two or more thereof.

The content of the filler (h) can be appropriately set according to its use. For example, in the case of separately packed curable composition, the content of the filler (h) is preferably 10 to 900 parts by mass, more preferably 40 to 400 parts by mass, and still more preferably 60 to 240 parts by mass based on 100 parts by mass in total of the polymerizable monomers contained in the first pack (A) and the second pack (B). Such a mode is preferred when the separately packed curable composition of the present invention is used as a dental adhesive resin cement, a dental composite resin or the like.

((i) Organic Solvent and/or (j) Water)

The curable composition of the present invention may contain an organic solvent (i). Examples of the organic solvent (i) include acetone, ethanol, isopropanol, tetrahydrofuran, acetonitrile, hexane, toluene, ethyl acetate, and dichloromethane. In the case of using the curable composition of the present invention for dental material applications, it is preferable to use water-soluble organic solvents, such as acetone, ethanol, and isopropanol, in view of adhesion and affinity with respect to a tooth surface. The water-soluble organic solvent is an organic solvent that forms a homogeneous solution with water at any ratio.

The curable composition of the present invention may contain (j) water. As water (j), it is preferable to use distilled water or ion-exchanged water so that there are no impurities that adversely affect the polymerization properties and adhesion.

When the organic solvent (i) is blended in the curable composition of the present invention, the content is preferably 5 to 95 parts by mass, more preferably 10 to 90 parts by mass, and still more preferably 20 to 75 parts by mass based on 100 parts by mass of a total of the polymerizable monomer, the organic solvent (i), and water (j) In such a mode, the homogeneousness, fluidity, and adhesive strength of the curable composition of the present invention can be improved.

When water (j) is blended in the curable composition of the present invention, the content is preferably 0.5 to 50 parts by mass, more preferably 1 to 40 parts by mass, and still more preferably 5 to 30 parts by mass based on 100 parts by mass of a total of the polymerizable monomer, the organic solvent (i), and water (j). In such a mode, the homogeneousness, fluidity, and adhesive strength of the curable composition of the present invention can be improved.

(Other Components)

The curable composition of the present invention may contain components other than those described above as appropriate and in accordance with the intended purpose as long as such components do not impair the storage stability and the curing function of the curable composition.

For example, the curable composition may contain various stabilizers, such as a polymerization inhibitor and an ultraviolet absorber, in order to improve storage stability and the like, and may contain known pigments, dyes, fluorescent agents, and the like, in order to adjust the color tone. In addition, the curable composition may contain a calcium-containing compound such as calcium chloride, a fluorine-containing compound such as sodium fluoride, an antifungal agent, an antibacterial agent, a therapeutic and biologically active ingredient. Furthermore, in order to improve the mechanical strength of the obtained cured product, the curable composition may contain a known reinforcing material such as fiber.

The content of each of the other components is preferably 0.00001 to 10 parts by mass, more preferably 0.00005 to 5 parts by mass, and still more preferably 0.0001 to 1 part by mass, based on 100 parts by mass of the polymerizable monomer, in view of exhibiting the characteristics of those other components and not impairing the effects of the present invention.

[Separately Packed Curable Composition]

The curable composition of the present invention may be divided and separately packaged in a plurality of packs such as (A) a first pack and (B) a second pack, that is, may be a separately packed curable composition. Examples of the form of those packs include pastes, liquids, and the like.

In view of ease of handling, both the first pack (A) and the second pack (B) are preferably pasty or liquid. When the curable composition of the present invention is a two-pack paste composition in which both the first pack (A) and the second pack (B) are pasty preparations, the curable composition is suitable for a dental adhesive resin cement. When the curable composition of the present invention is a two-pack liquid composition in which both the first pack (A) and the second pack (B) are liquid preparations, the curable composition is suitable for dental adhesive. The separately packed curable composition may have other packs such as (C) a third pack.

The curable composition of the present invention is usually composed of the first pack (A) and the second pack (B), and the components are stored separately in each preparation as necessary. The components to be included in the first pack (A) may be further separately packed in a plurality of packs. The component to be included in the second pack (B) may be further separately packed in a plurality of packs.

(First Pack (A))

The first pack (A) preferably contains the polymerizable monomer (a) having an acidic group and the transition metal compound (b). Moreover, because of including the polymerizable monomer (a) having an acidic group and the transition metal compound (b) in the first pack (A), performance is not impaired during storage and the component included in the second pack (B) is not adversely affected.

(Second Pack (B))

The second pack (B) preferably includes the at least one compound (c) selected from benzoxazole compounds and benzothiazole compounds, and the reducing agent (d) (for example, at least one compound (d1) selected from sulfinic acid and a salt thereof).

The polymerizable monomer (e) having no acidic group may be included in either one or both of the first pack (A) and the second pack (B) and is preferably included in both of those. When the polymerizable monomer (e) having no acidic group) is included in both the first pack (A) and the second pack (B), the polymerizable monomer included in the first pack (A) and the polymerizable monomer included in the second pack (B) may be the same or different.

When the peroxide (f) is included in the curable composition of the present invention, the peroxide (f) is preferably included in the second pack (B). By storing the peroxide (f) in the second pack (B), the components in the first pack (A) are not adversely affected during storage, and the activity thereof tends not to deteriorate during storage.

When the photopolymerization initiator (g) is included in the curable composition of the present invention, the photopolymerization initiator (g) is preferably included in the second pack (B) in view of storage stability. Further, it is also a preferable mode that the photopolymerization initiator (g) is included in a pack other than the first pack (A) or the second pack (B) (e.g., a third pack (C)). For example, when camphorquinone and an acylphosphine oxide compound are included as the photopolymerization initiator (g) in a third pack (C), the storage stability of the polymerizable monomer (e) having no acidic group that may be included in the second pack (B) during storage can further be improved.

The filler (h), the organic solvent (i), and water (j) may be included in either one or both of the first pack (A) and the second pack (B). When the filler (h) and/or the organic solvent (i) are included in both the first pack (A) and the second pack (B), the ingredients included in the first pack (A) and the ingredients included in the second pack (B) may be the same or different.

The mixing mass ratio between the first pack (A) and the second pack (B) can be appropriately set based on the curability of the polymerizable mixture to be obtained and the time available for the bonding operation (pot life), but it is preferably 1:10 to 10:1, more preferably 1:5 to 5:1, and further preferably 1:2 to 2:1.

A polymerizable mixture obtained by mixing each of the separate packs of the curable composition of the present invention can cure at 20 to 50° C., for example, in the vicinity of ordinary temperature or body temperature (37° C.), and the resulting cured product can be used for dental applications such as dental treatment. Further, the curable composition of the present invention can be cured even at ordinary temperature or higher. In one embodiment, the curable composition of the present invention can be cured at, for example, 10 to 120° C.

In addition, when the photopolymerization initiator (g) is included as a component of the curable composition, a desired cured product can be obtained by processing the polymerizable mixture obtained by mixing the separate packs into a predetermined shape, and then irradiating the mixture with visible light for a predetermined time using a known light irradiation device. The conditions such as the irradiation intensity and the irradiation time can be appropriately changed in accordance with the curability of the separately packed curable composition of the present invention. Moreover, the mechanical properties of the obtained cured product can also be improved by heat-treating the cured product after light irradiation under more appropriate conditions.

The curable composition of the present invention can be suitably used for dental applications such as various dental treatments. The curable composition of the present invention can be suitably used as, for example, a dental adhesive resin cement, a dental composite resin (including those having self-adhesive properties, the same applies hereinafter), a dental bonding material, a dental backing material, a dental root filler, an orthodontic adhesive, a mobile tooth fixing material, a tooth fovea fissure sealant (dental sealant), a temporary dental cement, a dental filler material, and the like.

The curable composition of the present invention can be used by a method generally known as a method of using a dental material. For example, when the separately packed curable composition of the present invention is used as a dental adhesive resin cement, a dental composite resin, or the like, the polymerizable mixture obtained by mixing the packs included in the separately packed curable composition can be applied alone to an adhesion surface. Further, when the curable composition of the present invention is used as the dental material, the curable composition may be used together with another dental material. For example, a polymerizable mixture prepared from the curable composition of the present invention can be applied after the surface of the adherend has been treated with another composition, such as a bonding material or a primer. Further, the curable composition of the present invention can be used as a bonding material by directly applying the curable composition to the surface of the adherend and then performing filling with another curable composition such as a dental composite resin.

The curable composition of the present invention has good polymerization properties. Further, a curable composition capable of providing a cured product having a sufficient mechanical strength can be prepared, even in the case where the curable composition is substantially free of a peroxide. Furthermore, a curable composition having excellent long-term storage stability at ordinary temperature or higher can also be prepared.

The curing time at 37° C. of the curable composition of the present invention is preferably 0.5 to 4 minutes, more preferably 0.8 to 3.5 minutes, and still more preferably 1 to 3 minutes. Further, the three-point bending strength of the cured product formed from the curable composition of the present invention is preferably 50 MPa or more, more preferably 70 MPa or more, and still more preferably 80 MPa or more. The three-point bending strength is preferably as high as possible, and the upper limit is not particularly limited, but may be 240 MPa, for example. Furthermore, the curing time at 37° C. of the curable composition of the present invention after storing at 55° C. for 3 weeks is preferably within 3 minutes, and more preferably from 1 to 3 minutes.

The curing time, the three-point bending strength, and the storage stability of the curable composition of the present invention are determined according to the methods described in Examples.

[Kit for Initiating Polymerization]

The above-described separately packed curable composition of the present invention can be used as a kit for initiating polymerization. That is, the kit for initiating polymerization of the present invention includes the first pack (A) and the second pack (B). The first pack (A) contains the polymerizable monomer (a) having an acidic group and the transition metal compound (b). The second pack (B) contains the at least one compound (c) selected from benzoxazole compounds and benzothiazole compounds and the reducing agent (d).

In the kit for initiating polymerization of the present invention, the first pack (A) and the second pack (B) are usually held in separate containers. Components to be included in the first pack (A) may be further separately packed in a plurality of packs. Components to be included in the second pack (B) may be further separately packed in a plurality of packs.

That is, components to be included in the first pack (A) may be held in the same container, or may be held in a separate container. For example, the polymerizable monomer (a) having an acidic group and the transition metal compound (b) to be included in the first pack (A) may be held in the same container, or may be held in separate containers. Further, components to be included in the second pack (B) may be held in the same container, or may be held in a separate container. For example, the compound (c) and the reducing agent (d) to be included in the second pack (B) may be held in the same container, or may be held in separate containers.

The kit for initiating polymerization of the present invention can be used for the same applications as the above-described curable composition of the present invention, and the preferred applications of the kit are also the same as those of the curable composition.

[Polymerization Initiator]

The second pack (B) in the above-described separately packed curable composition of the present invention may be used as a polymerization initiator. That is, the polymerization initiator of the present invention may include the at least one compound (c) selected from benzoxazole compounds and benzothiazole compounds and the reducing agent (d).

EXAMPLE

Hereinafter, the present invention will be described in detail with reference to examples and comparative examples, but the present invention is not limited to these examples.

The abbreviations of the compounds used in the examples are shown below.

[(a) Polymerizable Monomer Having an Acidic Group]
4-MET: 4-Methacryloyloxyethyl trimellitic acid (manufactured by Sun Medical Co., Ltd.)
MDP: 10-Methacryloyloxydecyl dihydrogen phosphate (manufactured by FUJIFILM Wako Pure Chemical Corporation)

[(b) Transition Metal Compound]
$VO(acac)_2$: Vanadyl(IV) acetylacetonate
(manufactured by Tokyo Chemical Industry Co., Ltd., used after pulverization by a mortar before use)
$V(acac)_3$: Vanadium(III) acetylacetonate
(manufactured by Sigma-Aldrich)
$Cu(OAc)_2$: Copper(II) acetate (manufactured by FUJIFILM Wako Pure Chemical Corporation)
CuCl: Copper(I) chloride (manufactured by FUJIFILM Wako Pure Chemical Corporation)
$CuCl_2$: Copper(II) chloride (manufactured by FUJIFILM Wako Pure Chemical Corporation)
$CuBr_2$: Copper(II) bromide (manufactured by Sigma-Aldrich)

[(c) at Least One Compound Selected from Benzoxazole Compounds and Benzothiazole Compounds]
HPBO: 2-(2-Hydroxyphenyl)benzoxazole
(manufactured by Tokyo Chemical Industry Co., Ltd.)
HPBT: 2-(2-Hydroxyphenyl)benzothiazole
(manufactured by Tokyo Chemical Industry Co., Ltd.)
BO: Benzoxazole (manufactured by Tokyo Chemical Industry Co., Ltd.)
BT: Benzothiazole (manufactured by FUJIFILM Wako Pure Chemical Corporation)
PBT: 2-Phenylbenzothiazole (manufactured by Tokyo Chemical Industry Co., Ltd.)
APBT: 2-(2-Aminophenyl)benzothiazole
(manufactured by Sigma-Aldrich)
[Benzimidazole Compound]
HPBI: 2-(2-Hydroxyphenyl)benzimidazole
(manufactured by Sigma-Aldrich)

[(d) Reducing Agent]
[(d1) at Least One Compound Selected from Sulfinic Acid and a Salt Thereof]
p-TSS: Sodium p-toluenesulfinate (manufactured by FUJIFILM Wako Pure Chemical Corporation, dried at 70° C. under reduced pressure after purchase, and pulverized by a mortar)
[Aromatic Amine Compound]
DEPT: N,N-Diethanol-p-toluidine
(manufactured by FUJIFILM Wako Pure Chemical Corporation)

[(e) Polymerizable Monomer Having No Acidic Group]
UDMA: 1,6-Bis(methacryloxyethyloxycarbonylamino)-2,2,4-trimethylhexane (self-prepared compound of HEMA and 2,2,4-trimethylhexyl diisocyanate in a 2:1 ratio in accordance with a known urethanization method) TEGDMA: Triethylene glycol dimethacrylate (manufactured by Shin Nakamura Chemical Co., Ltd.)
HEMA: 2-Hydroxyethyl methacrylate
(manufactured by Mitsubishi Chemical Corporation)
[(f) Peroxide]
TMBHP: 1,1,3,3-Tetramethylbutyl hydroperoxide (trade name "Luperox 215", manufactured by ARKEMA Yoshitomi Ltd.)
BPO: Benzoyl peroxide (manufactured by Tokyo Chemical Industry Co., Ltd.)
[(g) Photopolymerization Initiator]
CQ: d,l-Camphorquinone (manufactured by FUJIFILM Wako Pure Chemical Corporation)
DMABAE: Ethyl N,N-dimethylaminobenzoate
(manufactured by FUJIFILM Wako Pure Chemical Corporation)
[(h) Filler]
F1: Silane-treated barium glass powder, silane-treated fluoroaluminosilicate powder, etc. (trade names "GM8235", "G018-117", etc., manufactured by SCHOTT)
R812: Fine particle silica
(trade name "AEROSIL R812", manufactured by Nippon Aerosil Co., Ltd.)

[(i) Organic Solvent]
Acetone: Acetone (manufactured by FUJIFILM Wako Pure Chemical Corporation)
EtOH: Ethanol (manufactured by FUJIFILM Wako Pure Chemical Corporation)
[(j) Water]
Distilled water: manufactured using distilled water production equipment (manufactured by Tokyo Rikakikai Co., Ltd.)
[Other Components: Polymerization Inhibitor]
BHT: 2,6-Di-t-butyl-4-methylphenol
(manufactured by Tokyo Chemical Industry Co., Ltd.)
MEHQ: 4-Methoxyphenol (manufactured by FUJIFILM Wako Pure Chemical Corporation)

The first pack (A) and the second pack (B) were prepared by mixing the components in accordance with the formulations shown in the following Tables 1 and 2 (the numerical values in the table are in parts by mass), and a separately packed curable composition was thus produced that had a total mass ratio between the first pack and the second pack of 1:1.

TABLE 1

| (A) First pack | | A-1 | A-2 | A-3 | A-4 | A-5 | A-6 | A-7 | A-8 | A-9 | A-10 | A-11 |
|---|---|---|---|---|---|---|---|---|---|---|---|---|
| (e) Polymerizable monomer having no acidic group | UDMA | 60 | 60 | 60 | 60 | 60 | 60 | 60 | 60 | 60 | 60 | 60 |
| | TEGDMA | | | | | | | | | | | |
| | HEMA | 20 | 20 | 20 | 20 | 20 | 20 | 20 | 20 | 20 | 20 | 20 |
| (a) Polymerizable monomer having an acidic group | 4-MET | 20 | 20 | 20 | 20 | 20 | 20 | 20 | 20 | | | |
| | MDP | | | | | | | | | 20 | 20 | 20 |
| (b) Transition metal compound | VO(acac)$_2$ | 0.3 | 0.1 | | | | | | | | | |
| | V(acac)$_3$ | | | 0.6 | | | | | | | | |
| | Cu(OAc)$_2$ | | | | 0.3 | | | | | 0.6 | | |
| | CuCl | | | | | 0.5 | 0.07 | | | | 0.06 | 0.08 |
| | CuCl$_2$ | | | | | | | 0.1 | 0.08 | | | |
| | CuBr$_2$ | | | | | | | | | | | |
| (f) Peroxide | BPO | | | | | | | | | | | |
| (h) Filler | R812 | 5 | 5 | 5 | 5 | 5 | 5 | 5 | 5 | 5 | 5 | 5 |
| | F1 | 180 | 180 | 180 | 180 | 180 | 180 | 180 | 180 | 180 | 180 | 180 |
| Polymerization inhibitor | BHT | 0.2 | 0.2 | 0.2 | 0.2 | 0.2 | 0.2 | 0.2 | 0.2 | 0.2 | 0.2 | 0.2 |
| | MEHQ | 0.1 | 0.1 | 0.1 | 0.1 | 0.1 | 0.1 | 0.1 | 0.1 | 0.1 | 0.1 | 0.1 |

| (A) First pack | | A-12 | A-13 | A-14 | A-15 | A-16 | A-17 | A-18 | A-19 | A-20 |
|---|---|---|---|---|---|---|---|---|---|---|
| (e) Polymerizable monomer having no acidic group | UDMA | 60 | 60 | 60 | 60 | 60 | 60 | 60 | 60 | 60 |
| | TEGDMA | | | 20 | 20 | 20 | 20 | | | 20 |
| | HEMA | 20 | 20 | | | | | 20 | 20 | |
| (a) Polymerizable monomer having an acidic group | 4-MET | | | 20 | | 20 | | | | |
| | MDP | 20 | 20 | | 20 | | 20 | 20 | 20 | 20 |
| (b) Transition metal compound | VO(acac)$_2$ | | | | 0.3 | | | | | |
| | V(acac)$_3$ | | | | | | | | | |
| | Cu(OAc)$_2$ | | | 0.3 | | | | | | |
| | CuCl | | | | | | 0.1 | | | |
| | CuCl$_2$ | 0.06 | | | | 0.1 | | 0.06 | | 0.1 |
| | CuBr$_2$ | | 0.04 | | | | | | | |
| (f) Peroxide | BPO | | | | | | | | 0.5 | |
| (h) Filler | R812 | 5 | 5 | 5 | 5 | 5 | 5 | 5 | 5 | |
| | F1 | 180 | 180 | 180 | 180 | 180 | 180 | 180 | 180 | |
| Polymerization inhibitor | BHT | 0.2 | 0.2 | 0.2 | 0.2 | 0.2 | 0.2 | 0.2 | 0.2 | 0.2 |
| | MEHQ | 0.1 | 0.1 | 0.1 | 0.1 | 0.1 | 0.1 | 0.1 | 0.1 | 0.1 |

TABLE 2

| (B) Second pack | | B-1 | B-2 | B-3 | B-4 | B-5 | B-6 | B-7 | B-8 | B-9 | B-10 | B-11 | B-12 | B-13 | B-14 | B-15 | B-16 |
|---|---|---|---|---|---|---|---|---|---|---|---|---|---|---|---|---|---|
| (e) Polymerizable monomer having no acidic group | UDMA | 70 | 70 | 70 | 70 | 70 | 70 | 70 | 70 | 70 | 70 | 70 | 70 | | 30 | | 30 |
| | TEGDMA | 30 | 30 | 30 | 30 | 30 | 30 | 30 | 30 | 30 | 30 | 30 | 30 | | | | |
| | HEMA | | | | | | | | | | | | | | | | |
| (c) Compound (benzoxazole compound, | HPBO | 3 | | | | | | | 3 | | | | | | | | |
| | HPBT | | 3 | | | | | | | 3 | 3 | | | 3 | 3 | 3 | 3 |
| | BO | | | 3 | | | | | | | | | | | | | |

TABLE 2-continued

| (B) Second pack | | B-1 | B-2 | B-3 | B-4 | B-5 | B-6 | B-7 | B-8 | B-9 | B-10 | B-11 | B-12 | B-13 | B-14 | B-15 | B-16 |
|---|---|---|---|---|---|---|---|---|---|---|---|---|---|---|---|---|---|
| benzothiazole | BT | | | | 1 | | | | | | | | | | | | |
| compound) | PBT | | | | | 3 | | | | | | | | | | | |
| | APBT | | | | | | 3 | | | | | | | | | | |
| Benzimidazole compound | HPBI | | | | | | | | 3 | | | | | | | | |
| (d) Reducing agent sulfinic acid, a salt of sulfinic acid | p-TSS | 5 | 5 | 5 | 5 | 5 | 5 | 5 | 5 | 5 | 5 | 5 | 5 | 10 | 10 | 10 | 10 |
| (d) Reducing agent aromatic amine compound | DEPT | | | | | | | | | | | 0.2 | | | | | |
| (f) Peroxide | TMBHP | | | | | | | | | | | | 1 | | | | |
| (g) Photopolymerization initiator | CQ | | | | | | | | | 0.1 | 0.1 | | | | | | |
| | DMABAE | | | | | | | | | 0.6 | 0.6 | | | | | | |
| (h) Filler | R812 | 15 | 15 | 15 | 15 | 15 | 15 | 15 | 15 | 15 | 15 | 15 | 15 | | | | |
| | F1 | 165 | 165 | 165 | 165 | 165 | 165 | 165 | 165 | 165 | 165 | 165 | 165 | | | | |
| Polymerization inhibitor | BHT | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| | MEHQ | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| (i) Organic solvent | acetone | | | | | | | | | | | | | 80 | 50 | | |
| | EtOH | | | | | | | | | | | | | | | 80 | 50 |
| (j) Water | H$_2$O | | | | | | | | | | | | | 20 | 20 | 20 | 20 |

<Measurement Method of Curing Time (in Accordance with ISO 4049)>

The curing time in each examples and comparative examples were measured by differential thermal analysis using a differential scanning calorimeter (DSC). As the measuring apparatus, a DSC 3500 Sirius (manufactured by NETZSCH) was used.

Specifically, the first pack (A) and the second pack (B) in equal amounts (mass basis) were mixed on dental kneading paper with a dental spatula for 10 seconds at room temperature set to 20 to 25° C. to obtain a polymerizable mixture. The obtained polymerizable mixture was filled in a sample pan made of Al for DSC measurement.

The sample pan made of Al filled with the polymerizable mixture was placed in a DSC thermostat set at 37±1° C. just before measurement, and measurement was started 40 seconds after the start of kneading. The time until the point at which the temperature started to rise due to the start of the curing reaction of the polymerizable mixture and reached the maximum temperature was recorded as the curing time.

<Measurement Method of Three-Point Bending Strength (ISO 4049 Compliant)>

The first pack (A) and the second pack (B) in equal amounts (mass basis) were mixed on dental kneading paper with a dental spatula for 10 seconds at room temperature set to 20 to 25° C. to obtain a homogeneous polymerizable mixture. A 2 mm×2 mm×25 mm mold for test piece preparation was filled with the obtained polymerizable mixture and pressed from both sides with a Lumirror film, and the mixture was polymerized by a corresponding polymerization method.

When preparing a test piece only by chemical polymerization, a cured product obtained by causing polymerization in the mold filled with the polymerizable mixture for 1 hour within a thermostat set to 37±1° C. was used as the test piece.

When preparing a test piece by photopolymerization, a cured product obtained by irradiating with light on the back and front for 1 minute and 30 seconds at room temperature using a technical LED irradiator was used as the test piece.

The technical LED irradiator used was "Alpha Light V (manufactured by J. MORITA CORP./Light source: LED lamp, 400 to 408 nm; 465 to 475 nm)", which is a device having an irradiance of 60 mW/cm$^2$ from a light source at 405 nm and an accumulated light amount of 5,100 mJ/cm$^2$ for 1 minute 30 seconds as measured by the accumulated ultraviolet light meter "UIT-250/manufactured by USHIO INC.".

Each test piece was removed from the mold, immersed in distilled water, stored in a thermostat set to 37±1° C. for 18 hours. The test piece was then taken out, and the three-point bending fracture strength was measured using a universal testing machine (manufactured by Intesco Co., Ltd.). The fracture strength measurement test was carried out by applying a load until the test piece broke at a crosshead speed of 1 mm/min, and the strength of the cured product was calculated from the obtained maximum point stress. Further, in this test, the elastic modulus of the cured product obtained from the curable composition of the present invention was also calculated. In addition, the measurement results of bending strength and the elastic modulus were calculated as an average value of measured values under the same condition.

<Storage Stability Test>

The curing time of the first pack (A) and the second pack (B) were measured immediately after preparation using the above-described method, and the first pack (A) and second pack (B) separately prepared from those used for measuring the curing time were stored for 3 weeks in a thermostat set to 55° C. Each of the first pack (A) and the second pack (B) was taken out after storing for two weeks and three weeks, and the curing time was measured in accordance with the method described above.

If the curing time is within 3 minutes, it can be determined that the tested polymerizable mixture has sufficient curability. Further, if the three-point bending strength of the obtained cured product is 80 MPa or more, it can be determined that the curable composition provides a cured product having a sufficient strength. Furthermore, if the curing time of the polymerizable mixture tested for the storage stability test is less than 3 minutes after the storage stability test, it can be determined that the curable composition maintains sufficient polymerization properties and the storage stability is excellent.

Examples 1 to 24, Comparative Examples 1 to 5

As shown in Table 3, the curing time was measured for each of the curable compositions of combinations of the first pack (A) and the second pack (B) prepared as in Tables 1 and 2 in accordance with the method described above.

TABLE 3

|  | (A) First pack | (B) Second pack | Curing time |
| --- | --- | --- | --- |
| Example 1 | A-1 | B-1 | 2.7 min |
| Example 2 | A-3 | B-1 | 2.8 min |
| Example 3 | A-5 | B-1 | 1.5 min |
| Example 4 | A-7 | B-1 | 2.3 min |
| Example 5 | A-9 | B-1 | 2.3 min |
| Example 6 | A-11 | B-1 | 1.3 min |
| Example 7 | A-12 | B-1 | 1.3 min |
| Example 8 | A-1 | B-2 | 3.0 min |
| Example 9 | A-4 | B-2 | 2.0 min |
| Example 10 | A-6 | B-2 | 1.5 min |
| Example 11 | A-8 | B-2 | 2.8 min |
| Example 12 | A-9 | B-2 | 2.5 min |
| Example 13 | A-10 | B-2 | 2.2 min |
| Example 14 | A-12 | B-2 | 1.0 min |
| Example 15 | A-13 | B-2 | 1.5 min |
| Example 16 | A-12 | B-3 | 1.2 min |
| Example 17 | A-12 | B-4 | 1.0 min |
| Example 18 | A-12 | B-5 | 1.1 min |
| Example 19 | A-12 | B-6 | 1.1 min |
| Example 20 | A-2 | B-10 | 1.4 min |
| Example 21 | A-20 | B-13 | 2.2 min |
| Example 22 | A-20 | B-14 | 1.6 min |
| Example 23 | A-20 | B-15 | 2.7 min |
| Example 24 | A-20 | B-16 | 2.0 min |
| Comparative Example 1 | A-18 | B-2 | >10 min |
| Comparative Example 2 | A-1 | B-12 | 5.0 min |
| Comparative Example 3 | A-2 | B-12 | 8.8 min |

TABLE 3-continued

|  | (A) First pack | (B) Second pack | Curing time |
| --- | --- | --- | --- |
| Example 3 Comparative Example 4 | A-12 | B-7 | 4.2 min |
| Comparative Example 5 | A-19 | B-11 | 4.1 min |

Examples 1 to 19 free of peroxide (f) indicated good curing times. On the other hand, Comparative Example 1 free of the transition metal compound (b) did not cure within 10 minutes and Comparative Examples 2 and 3 free of the at least one compound (c) selected from benzoxazole compounds and benzothiazole compounds exhibited poor polymerization properties. In Comparative Example 4 obtained by using a benzimidazole compound which is not the compound (c), a sufficient polymerization promotion effect was not obtained. Further, the curable composition containing a peroxide-based chemical polymerization initiator with a small amount of peroxide (f) such as Comparative Example 5 did not show sufficient polymerization properties.

In Example 20, in which the peroxide (f) was blended, the polymerization properties were improved. Furthermore, in Examples 21 to 24 in which the organic solvent (i) and water (j) were blended, good curing times were obtained.

Examples 25 to 37, Comparative Example 6

As shown in Table 4, the three-point bending strength and the elastic modulus were measured for each of the curable compositions of combinations of the first pack (A) and the second pack (B) prepared as in Tables 1 and 2 in accordance with the method described above. The standard deviation of each measurement result is described in parentheses in Table 4.

TABLE 4

|  | (A) First pack | (B) Second pack | Polymerization method | Bending strength | Elastic modulus |
| --- | --- | --- | --- | --- | --- |
| Example 25 | A-14 | B-1 | SC | 80.8 MPa (8.3) | 3.3 GPa (0.3) |
| Example 26 | A-16 | B-1 | SC | 96.5 MPa (11.3) | 3.6 GPa (1.0) |
| Example 27 | A-17 | B-1 | SC | 95.7 MPa (5.8) | 4.7 GPa (0.1) |
| Example 28 | A-14 | B-2 | SC | 87.9 MPa (4.9) | 3.5 GPa (0.3) |
| Example 29 | A-15 | B-2 | SC | 98.1 MPa (13.8) | 4.9 GPa (0.9) |
| Example 30 | A-16 | B-2 | SC | 82.9 MPa (5.2) | 3.3 GPa (0.3) |
| Example 31 | A-17 | B-2 | SC | 101.9 MPa (7.0) | 5.0 GPa (0.2) |
| Example 32 | A-14 | B-8 | DC | 108.3 MPa (9.1) | 5.7 GPa (0.6) |
| Example 33 | A-15 | B-8 | DC | 108.2 MPa (1.3) | 5.4 GPa (0.3) |
| Example 34 | A-17 | B-8 | DC | 105.8 MPa (14.1) | 5.5 GPa (0.3) |
| Example 35 | A-14 | B-9 | DC | 128.9 MPa (5.2) | 6.4 GPa (0.1) |
| Example 36 | A-15 | B-9 | DC | 111.4 MPa (4.3) | 5.6 GPa (0.6) |
| Example 37 | A-17 | B-9 | DC | 104.0 MPa (5.8) | 6.1 GPa (0.3) |
| Comparative Example 6 | A-19 | B-11 | SC | 75.8 MPa (13.8) | 3.1 GPa (1.1) |

*SC: Single Cure (Chemical polymerization), DC: Dual Cure(Combination of chemical polymerization and photopolymerization)

The cured products of Examples 25 to 31, which was cured by chemical polymerization, showed good mechanical strength. Further, the cured products of Examples 32 to 37, which were dual cure materials containing the photopolymerization initiator (g), also showed a sufficient mechanical strength. On the other hand, the mechanical strength of a cured product formed from a curable composition containing a peroxide-based chemical polymerization initiator with a small amount of peroxide (f) such as Comparative Example 6 was low as compared with Examples 25 to 37.

Examples 38 to 44

As shown in Table 5, the storage stability was evaluated for each of the curable compositions of combinations of the first pack (A) and the second pack (B) prepared as in Tables 1 and 2 with the method described hereinbefore. The curable compositions prepared in Examples 38 to 44 maintained sufficient polymerization properties after storage at 55° C. for 3 weeks, and showed excellent storage stability.

TABLE 5

|  | Example 38 | Example 39 | Example 40 | Example 41 | Example 42 | Example 43 | Example 44 |
|---|---|---|---|---|---|---|---|
| (A) First pack | A-11 | A-11 | A-12 | A-12 | A-12 | A-12 | A-6 |
| (B) Second pack | B-1 | B-3 | B-2 | B-3 | B-4 | B-6 | B-2 |
| Curing time |  |  |  |  |  |  |  |
| Immediately after preparation | 1.3 min | 1.0 min | 1.0 min | 1.2 min | 1.0 min | 1.1 min | 1.5 min |
| At 55° C. after 2 weeks | 2.5 min | 1.4 min | 1.0 min | 2.5 min | 1.2 min | 2.1 min | 1.9 min |
| At 55° C. after 3 weeks | 1.9 min | 1.6 min | 2.0 min | 1.7 min | 1.0 min | 1.5 min | 1.9 min |

The invention claimed is:

1. A polymerization initiator comprising:
   (c) at least one compound selected from the group consisting of benzoxazole, benzothiazole, and compounds represented by following Formula (1),

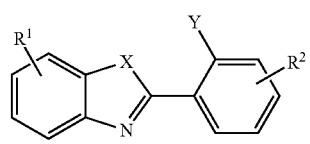

where X represents an oxygen atom or a sulfur atom, Y represents a hydroxyl group or an amino group, and $R^1$ and $R^2$ each independently represent a hydrogen atom, a halogen atom, or a hydrocarbon group having 1 to 4 carbon atoms; and
   (d) a reducing agent comprising at least one compound selected from the group consisting of sulfinic acid, a salt of sulfinic acid, ascorbic acid, and a salt of ascorbic acid.

2. A kit for initiating polymerization, comprising (A) a first pack and (B) a second pack:
   (A) the first pack containing:
      (a) a polymerizable monomer having an acidic group, and
      (b) a transition metal compound; and
   (B) the second pack containing the polymerization initiator according to claim 1.

3. A curable composition comprising:
   (a) a polymerizable monomer having an acidic group;
   (b) a transition metal compound; and
   the polymerization initiator according to claim 1.

4. The kit for initiating polymerization according to claim 2, wherein the compound (c) does not include a compound having a mercapto group at the 2-position of a benzoxazole ring or a compound having a mercapto group at the 2-position of a benzothiazole ring.

5. The kit for initiating polymerization according to claim 2, wherein the reducing agent (d) comprises at least one compound selected from sulfinic acid, a salt of sulfinic acid, ascorbic acid, and a salt of ascorbic acid.

6. The kit for initiating polymerization according to claim 2, wherein the transition metal compound (b) is at least one selected from copper compounds and vanadium compounds.

7. The kit for initiating polymerization according to claim 2, further comprising:
   (e) a polymerizable monomer having no acidic group.

8. The kit for initiating polymerization according to claim 2, wherein the kit for initiating polymerization is substantially free of (f) a peroxide.

9. The kit for initiating polymerization according to claim 2, further comprising:
   (f) a peroxide.

10. The kit for initiating polymerization according to claim 9, wherein the peroxide (f) is at least one selected from hydroperoxide compounds and peroxyester compounds.

11. The kit for initiating polymerization according to claim 2, further comprising:
   at least one selected from (g) a photopolymerization initiator, (h) a filler, (i) an organic solvent, and (j) water.

12. The kit for initiating polymerization according to claim 2, wherein a total of the transition metal compound (b), the compound (c), and the reducing agent (d) is 0.1 to 40 parts by mass, based on 100 parts by mass of polymerizable monomers.

13. The kit for initiating polymerization according to claim 2, wherein a content of the transition metal compound (b) is 0.001 to 5 parts by mass, based on 100 parts by mass of polymerizable monomers.

14. The kit for initiating polymerization according to claim 2, wherein a content of the compound (c) is 0.1 to 20 parts by mass, based on 100 parts by mass of polymerizable monomers.

15. The kit for initiating polymerization according to claim 2, wherein a content of the reducing agent (d) is 0.01 to 20 parts by mass, based on 100 parts by mass of polymerizable monomers.

16. The kit for initiating polymerization according to claim 2, wherein the kit for initiating polymerization is for dental use.

17. A dental composition comprising the kit for initiating polymerization according to claim 2,
   wherein the dental composition is a dental adhesive resin cement, a dental composite resin, a dental bonding material, a dental backing material, a dental root filler, an orthodontic adhesive, a mobile tooth fixing material, a dental sealant, a temporary dental cement, or a dental filler material.

18. A cured product of the kit for initiating polymerization according to claim 2.

19. A cured product of the dental composition according to claim 17.

* * * * *